(12) United States Patent
Mochizuki

(10) Patent No.: US 10,986,458 B2
(45) Date of Patent: Apr. 20, 2021

(54) INFORMATION PROCESSING APPARATUS AND INFORMATION PROCESSING METHOD

(71) Applicant: SONY CORPORATION, Tokyo (JP)

(72) Inventor: Daisuke Mochizuki, Chiba (JP)

(73) Assignee: SONY CORPORATION, Tokyo (JP)

(*) Notice: Subject to any disclaimer, the term of this patent is extended or adjusted under 35 U.S.C. 154(b) by 10 days.

(21) Appl. No.: 16/341,721

(22) PCT Filed: Oct. 17, 2017

(86) PCT No.: PCT/JP2017/037505
§ 371 (c)(1),
(2) Date: Apr. 12, 2019

(87) PCT Pub. No.: WO2018/092486
PCT Pub. Date: May 24, 2018

(65) Prior Publication Data
US 2020/0053501 A1 Feb. 13, 2020

(30) Foreign Application Priority Data
Nov. 16, 2016 (JP) .............................. JP2016-223275

(51) Int. Cl.
*H04S 7/00* (2006.01)
*G10L 19/008* (2013.01)
(Continued)

(52) U.S. Cl.
CPC ............ *H04S 7/303* (2013.01); *G10L 19/008* (2013.01); *H04R 5/02* (2013.01); *H04R 5/04* (2013.01);
(Continued)

(58) Field of Classification Search
CPC .......... G06F 3/012; G06F 3/011; H04S 7/303; H04S 3/008; H04S 2400/11;
(Continued)

(56) References Cited

U.S. PATENT DOCUMENTS 3,712,292 A * 1/1973 Zentmeyer, Jr. ...... A61M 21/00
600/28
2004/0075677 A1 * 4/2004 Loyall .................... G06F 3/011
715/706
(Continued)

FOREIGN PATENT DOCUMENTS

CN 102855116 A 1/2013
CN 105578355 A 5/2016
(Continued)

OTHER PUBLICATIONS

International Search Report and Written Opinion of PCT Application No. PCT/JP2017/037505, dated Dec. 12, 2017, 08 pages of ISRWO.
(Continued)

*Primary Examiner* — Davetta W Goins
*Assistant Examiner* — Kuassi A Ganmavo
(74) *Attorney, Agent, or Firm* — Chip Law Group

(57) ABSTRACT

An information processing apparatus includes: an action recognition unit; an audio data selection unit; and an audio information generation unit, in which the action recognition unit is configured to recognize an action pattern of a user on the basis of sensor information. The audio data selection unit is configured to select audio data corresponding to the action pattern of the user recognized by the action recognition unit. The audio information generation unit generates, on the basis of the audio data selected by the audio data selection unit, multichannel audio information for localizing a sound image of a sound source in real space around the user. The
(Continued)

| Stationary | Walking | Running |
|---|---|---|
| ma001.mp3 | mb001.mp3 | mc001.mp3 |
| ma002.mp3 | mb002.mp3 | mc002.mp3 |
| ... | ... | ... |

| Small degree of fatigue | Medium degree of fatigue | Large degree of fatigue |
|---|---|---|
| ta001.mp3 | tb001.mp3 | tc001.mp3 |
| ta002.mp3 | tb002.mp3 | tc002.mp3 |
| ... | ... | ... | information processing apparatus makes it possible to achieve augmented reality that follows a qualitative change in the action of the user.

16 Claims, 9 Drawing Sheets

(51) Int. Cl.
| | | |
|---|---|---|
| H04R 5/02 | (2006.01) | |
| H04R 5/04 | (2006.01) | |
| H04S 3/00 | (2006.01) | |
| G06F 3/01 | (2006.01) | |
| A61B 5/024 | (2006.01) | |
| G06T 19/00 | (2011.01) | |
| G10H 1/40 | (2006.01) | |

(52) U.S. Cl.
CPC .............. *H04S 3/008* (2013.01); *A61B 5/024* (2013.01); *G06F 3/011* (2013.01); *G06F 3/012* (2013.01); *G06T 19/006* (2013.01); *G10H 1/40* (2013.01); *H04S 2400/01* (2013.01); *H04S 2400/11* (2013.01); *H04S 2420/01* (2013.01)

(58) Field of Classification Search
CPC ..... H04S 2420/01; G10L 19/008; H04R 5/02; H04R 5/04; G06T 19/006; A61B 5/024; G10H 1/40; G03F 3/012
See application file for complete search history.

(56) References Cited

U.S. PATENT DOCUMENTS

| | | | | |
|---|---|---|---|---|
| 2006/0243120 A1* | 11/2006 | Takai | ................... | G06F 16/636 84/612 |
| 2007/0169614 A1* | 7/2007 | Sasaki | ................ | A63B 69/0028 84/612 |
| 2008/0228299 A1 | 9/2008 | Ikeda et al. | | |
| 2008/0254946 A1* | 10/2008 | Pauws | ................ | A63B 71/0686 482/8 |
| 2009/0205482 A1* | 8/2009 | Shirai | ................ | A63B 71/0686 84/612 |
| 2010/0049074 A1* | 2/2010 | Cortenraad | ........... | G06F 16/636 600/544 |
| 2010/0095209 A1* | 4/2010 | Gupta | ................... | A43B 3/0021 715/716 |
| 2010/0321519 A1* | 12/2010 | Bill | ........................ | G06F 16/639 348/222.1 |
| 2012/0314871 A1* | 12/2012 | Koga | ...................... | H04S 7/304 381/17 |
| 2013/0006064 A1* | 1/2013 | Reiner | ................. | A61B 5/0022 600/300 |
| 2014/0079225 A1* | 3/2014 | Jarske | .................... | H04R 29/00 381/56 |
| 2014/0281971 A1* | 9/2014 | Isbell, III | ......... | H04N 21/42202 715/716 |
| 2014/0306866 A1* | 10/2014 | Miller | ....................... | G06T 1/20 345/8 |
| 2014/0347368 A1* | 11/2014 | Kishore | ................. | G06T 13/00 345/473 |
| 2015/0104049 A1* | 4/2015 | Noda | ...................... | G06F 3/012 381/303 |
| 2015/0117664 A1* | 4/2015 | Mossner | .............. | H04R 1/1091 381/74 |
| 2016/0026856 A1* | 1/2016 | Wisbey | .............. | G06F 19/3481 700/91 |
| 2016/0030809 A1* | 2/2016 | Wisbey | .............. | A61B 5/02416 600/301 |
| 2016/0055420 A1* | 2/2016 | Karanam | ............... | A61B 5/165 700/52 |
| 2017/0078825 A1* | 3/2017 | Mangiat | ................... | H04S 7/304 |
| 2017/0339503 A1* | 11/2017 | Lyren | ..................... | H04S 7/302 |

FOREIGN PATENT DOCUMENTS

| | | | |
|---|---|---|---|
| EP | 3067781 A1 | 9/2016 | |
| JP | 2007328568 A | * 12/2007 | |
| JP | 2008-226400 A | 9/2008 | |
| JP | 2011167549 A | * 9/2011 | |
| JP | 2013-005021 A | 1/2013 | |
| JP | 2013-167941 A | 8/2013 | |
| WO | WO-2014171200 A1 | * 10/2014 | ........... A63F 13/215 |
| WO | 2016/002318 A1 | 1/2016 | |

OTHER PUBLICATIONS

Office Action for CN Patent Application No. 201780069477.7, dated Sep. 2, 2020, 12 pages of Office Action and 17 pages of English Translation.

* cited by examiner user  Virtual object user  Virtual object

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/037505 filed on Oct. 17, 2017, which claims priority benefit of Japanese Patent Application No. JP 2016-223275 filed in the Japan Patent Office on Nov. 16, 2016. Each of the above-referenced applications is hereby incorporated herein by reference in its entirety.

TECHNICAL FIELD

The present technology relates to improvement of quality of augmented reality.

BACKGROUND ART

In the technical field of wearable computing, there is already known a technology for estimating, when a user wearing a wearable computer moves, the amount of spatial displacement of the user by a sensor device included in the wearable computer (see, for example, Patent Literature 1).

Patent Literature 1 discloses also a technology regarding generation of multichannel audio information. The technology described in Patent Literature 1 is to synthesize audio so that the sound can be perceived as if it were emitted from a spatial position, and particularly to synthesize audio so that the sound can be perceived as if the spatial position from which the sound was emitted did not change even when a user changes the position or orientation.

Patent Literature 2 discloses a technology for displaying, when a person acts, a virtual object relating to information regarding a past action of a different person by using information regarding an actual past action of the different person. The application example disclosed in Patent Literature 2 shows an example in which a running image of another person who has run the same course is displayed on an eyeglass-type display apparatus during running.

CITATION LIST

Patent Literature

Patent Literature 1: Japanese Patent Application Laid-open No. 2013-005021
Patent Literature 2: Japanese Patent Application Laid-open No. 2013-167941

DISCLOSURE OF INVENTION

Technical Problem

In the technical field of providing augmented reality to a user by using a wearable computer, it is desired to provide a more realistic presentation. However, the preceding examples described above have not focus on the content of the user's action to provide augmented reality. For example, even when the content of the action changes from a "walking" action to a "running" action or changes from a "light-fatigue" exercise to a "heavy-fatigue" exercise, output following a qualitative change in the action has not been performed.

In view of the circumstances as described above, it is an object of the present technology to provide an information processing apparatus that makes it possible to achieve augmented reality following a qualitative change in an action of a user.

Solution to Problem

In order to achieve the above-mentioned object, an information processing apparatus according to an aspect of the present technology includes an action recognition unit; an audio data selection unit; and an audio information generation unit.

The action recognition unit is configured to recognize an action pattern of a user on the basis of sensor information.

The audio data selection unit is configured to select audio data corresponding to the action pattern of the user recognized by the action recognition unit.

The audio information generation unit generates, on the basis of the audio data selected by the audio data selection unit, multichannel audio information for localizing a sound image of a sound source in real space around the user.

In accordance with the information processing apparatus according to an aspect of the present technology, it is possible to provide augmented reality following a qualitative change in an action of a user to the user.

The audio data selection unit may be configured to select the audio data as audio emitted from a virtual object to be placed in the real space.

In this case, the audio information generation unit may be configured to perform sound image localization by generating the multichannel audio information, the virtual object being placed at a position of the sound source by the sound image localization.

The audio data selection unit may be configured to select, when audio data to be selected is changed as a result of recognition by the action recognition unit, both audio data corresponding to a switching pattern of audio data from that before the change to that after the change, and the audio data after the change.

The audio data selection unit may be configured to select, when audio data to be selected is changed as a result of recognition by the action recognition unit, audio data that matches with information associated with the virtual object where there is a plurality of pieces of audio data corresponding to an action pattern of the user.

The information processing apparatus may further include a displacement calculation unit that outputs, on the basis of the sensor information, user displacement including a relative change in a position of the user.

The audio information generation unit may be configured to modulate, on the basis of the user displacement output by the displacement calculation unit, the audio data selected by the audio data selection unit, thereby to generate the multichannel audio information.

The audio information generation unit may be configured to modulate the audio data selected by the audio data selection unit so that the sound source whose sound image is localized by the multichannel audio information is placed at a position following the user displacement output by the displacement calculation unit, thereby to generate the multichannel audio information.

The audio information generation unit may be configured to generate the multichannel audio information so that the sound source whose sound image is localized by the multichannel audio information follows a position in space with a time delay, the position starting from a position of the user identified by the user displacement.

The audio information generation unit may be configured to generate, on the basis of the user displacement output by the displacement calculation unit and map information including position coordinates of a building acquired from outside, the multichannel audio information so that the virtual object is not placed in a range of the position coordinates of the building included in the map information.

The audio information generation unit may be configured to generate, where the range of the position coordinates of the building included in the map information overlaps with a position where the virtual object is placed, the multichannel audio information including a collision sound.

The information processing apparatus may further include a state analysis unit configured to analyze a changeable state of the user in accordance with one of the action pattern of the user recognized by the action recognition unit and the sensor information.

The audio data selection unit may be configured to select audio data corresponding to the action pattern of the user and audio data corresponding to the state of the user analyzed by the state analysis unit.

The audio information generation unit may be configured to synthesize the audio data corresponding to the action pattern of the user selected by the audio data selection unit and the audio data corresponding to the state of the user, thereby to generate the multichannel audio information on the basis of the synthesized audio data.

The state analysis unit may be configured to assign a degree of fatigue per unit time in accordance with one of the action pattern of the user recognized by the action recognition unit and the sensor information, and accumulate the assigned degree of fatigue per unit time, thereby to calculate the degree of fatigue as the state of the user.

The audio data selection unit may be configured to select, where the action pattern of the user recognized by the action recognition unit continues exceeding a predetermined threshold value, audio data different from the audio data corresponding to the action pattern of the user recognized by the action recognition unit.

An information processing method according to another aspect of the present technology includes an action recognition step; an audio data selection step; and an audio information generation step.

In the action recognition step, an action pattern of a user is recognized on the basis of sensor information.

In the audio data selection step, audio data corresponding to the action pattern of the user recognized by the action recognition step is selected.

In the audio information generation step, on the basis of the audio data selected by the audio data selection step, multichannel audio information for localizing a sound image of a sound source is generated in real space around the user.

A program according to still another aspect of the present technology causes a computer to execute an action recognition step; an audio data selection step; and an audio information generation step.

In the action recognition step, an action pattern of a user is recognized on the basis of sensor information.

In the audio data selection step, audio data corresponding to the action pattern of the user recognized by the action recognition step is selected.

In the audio information generation step, on the basis of the audio data selected by the audio data selection step, multichannel audio information for localizing a sound image of a sound source is generated in real space around the user.

Advantageous Effects of Invention

As described above, in accordance with the present technology, it is possible to achieve augmented reality following a qualitative change in an action of a user.

It should be noted that the above-mentioned effect is not necessarily limitative, and any effect described in the present specification or other effects that can be grasped from the present specification may be exerted in addition to or instead of the above-mentioned effect.

MODE(S) FOR CARRYING OUT THE INVENTION

Figure 1A:
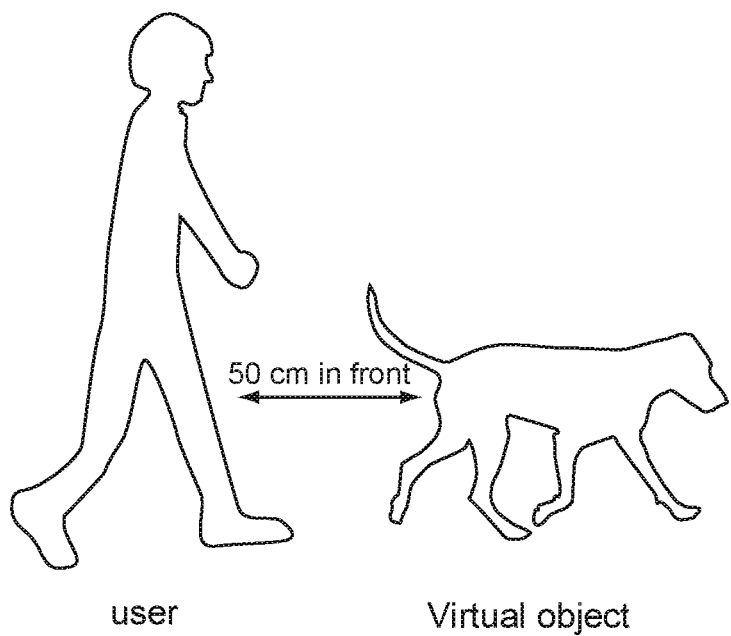
FIGS. 1A and 1B are diagrams (part 1) showing an example of augmented reality provided to a user as a result of output by an information processing apparatus according to an embodiment of the present technology.

Hereinafter, favorable embodiments of the present technology will be described in detail with reference to the drawings. It should be noted that the components having substantially the same functional configuration will be denoted by the same reference symbols, and duplicate description will be omitted in the present specification and in the drawings.

Note that descriptions will be made in the following order.
1. Outline of Information Processing Apparatus according to Embodiment of Present Technology
2. Configuration
2-1. External Configuration
2-2. Internal Configuration
3. Operation
4. Conclusion
5. Other Embodiments
5-1. Another Embodiment 1
5-2. Another Embodiment 2
5-3. Another Embodiment 3
5-4. Another Embodiment 4
5-5. Another Embodiment 5

5-6. Another Embodiment 6
5-7. Another Embodiment 7
6. Appendix

<1. Outline of Information Processing Apparatus according to Embodiment of Present Technology>

FIGS. 1A 1B, 2A, and 2B are each a diagram showing an example of augmented reality provided to a user as a result of output by an information processing apparatus 1 according to this embodiment. The information processing apparatus 1 outputs multichannel audio information in which a sound image is localized so that a sound can be heard from a particular direction around a user. The sound image localization is performed by, for example, adjusting the volume of sounds entering each of right and left ears.

Figure 1B:
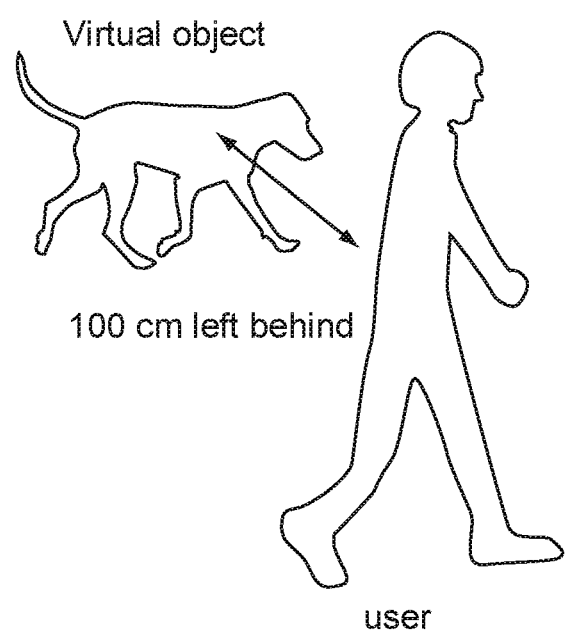
Figure 2A:
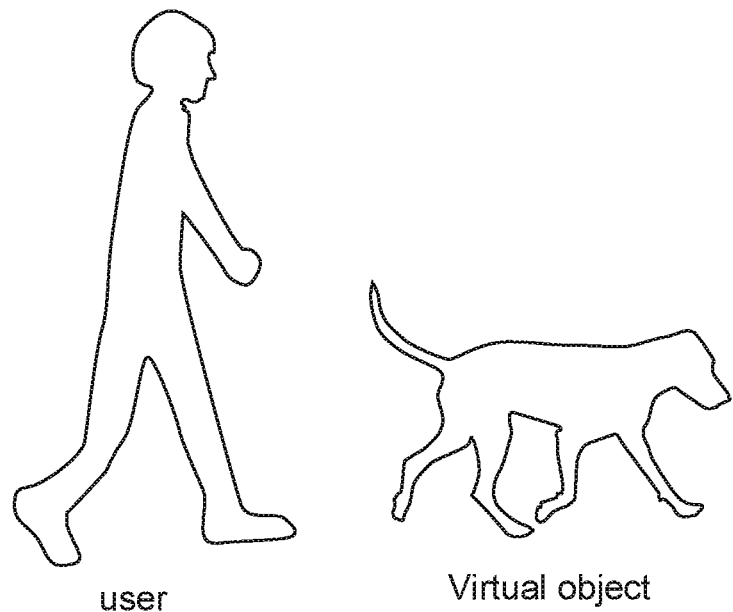
FIGS. 2A and 2B are diagrams (part 2) showing an example of augmented reality provided to a user as a result of output by the information processing apparatus according to the embodiment of the present technology.
Figure 2B:
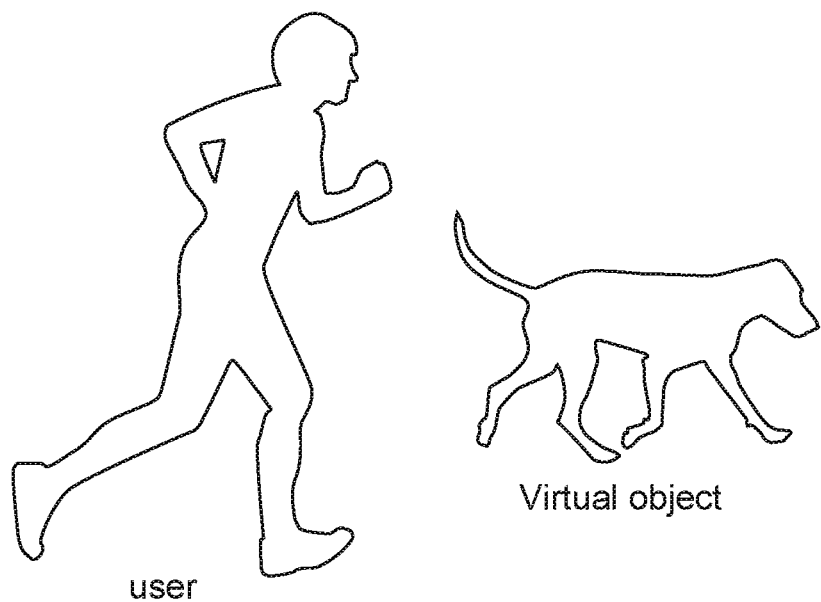

FIG. 1A shows the state where a virtual dog as an example of a virtual object is walking 50 cm in front of a user. Footsteps and breath sounds of the dog are multi-channeled, and the volume of the sounds entering the right and left ears or the effect are adjusted, thereby providing the augmented reality as shown in the figure to the user. Here, the balance between the right and left volumes in the multichannel audio information is changed, which gives a feeling as if the virtual object were walking at the position 100 cm left behind as shown in FIG. 1B.

Such a sound image localization technology allows a user to feel the presence of the virtual object to a certain degree. Meanwhile, it is unnatural if there is no change in the audio emitted from the virtual object when a qualitative change in an action of the user occurs or a change in the state of the user occurs. For example, in the case where the state of the user changes from the walking state FIG. 2A) to the running state (FIG. 2B), it is unnatural if the virtual object simulated as a dog follows the user with the same breath sound as that when walking. Similarly, it is unnatural if the virtual object seems to be not tired at all even after running for a long time with the user.

In view of the above, in this embodiment described below, in order to provide augmented reality having higher quality, augmented reality follows a qualitative change in the action of the user.

Here, the qualitative change includes a change in the type ("running" and "walking", etc.) of the action of the user. In the existing wearable computing, the system has been capable of grasping that the action of the user is "moving", by a method such as absolute position measurement. However, in the case where the action has changed from the type of action "walking" to the type of action "running", the follow-up to the qualitative change has been insufficient. For that reason, there has been a possibility that augmented reality that makes the user feel uncomfortable is provided.

In the case where the virtual object is regarded as a virtually-present character as an example, the augmented reality to be provided to the user needs to change depending on the type of the action of the character. For example, there is a possibility that the user feels uncomfortable if the footsteps when the character is running and the footsteps when the character is walking differ although both of them are "footsteps".

In this embodiment, augmented reality that follows a qualitative change in the action of a user by recognizing an action pattern of the user on the basis of sensor information input from a sensor 101, selecting audio data corresponding to the recognized action pattern, and then displacing the selected audio data is provided to the user.

Note that in the following description, a virtual dog is used as an example of the virtual object. Further, an application that allows the user to walk with the virtual dog by wearing the information processing apparatus 1 as the entire application will be described as an example.

The outline of the information processing apparatus 1 according to this embodiment has been described heretofore. Next, a configuration of the information processing apparatus 1 will be described with reference to FIG. 3 and FIG. 4.

2-1. External Configuration

Figure 3:
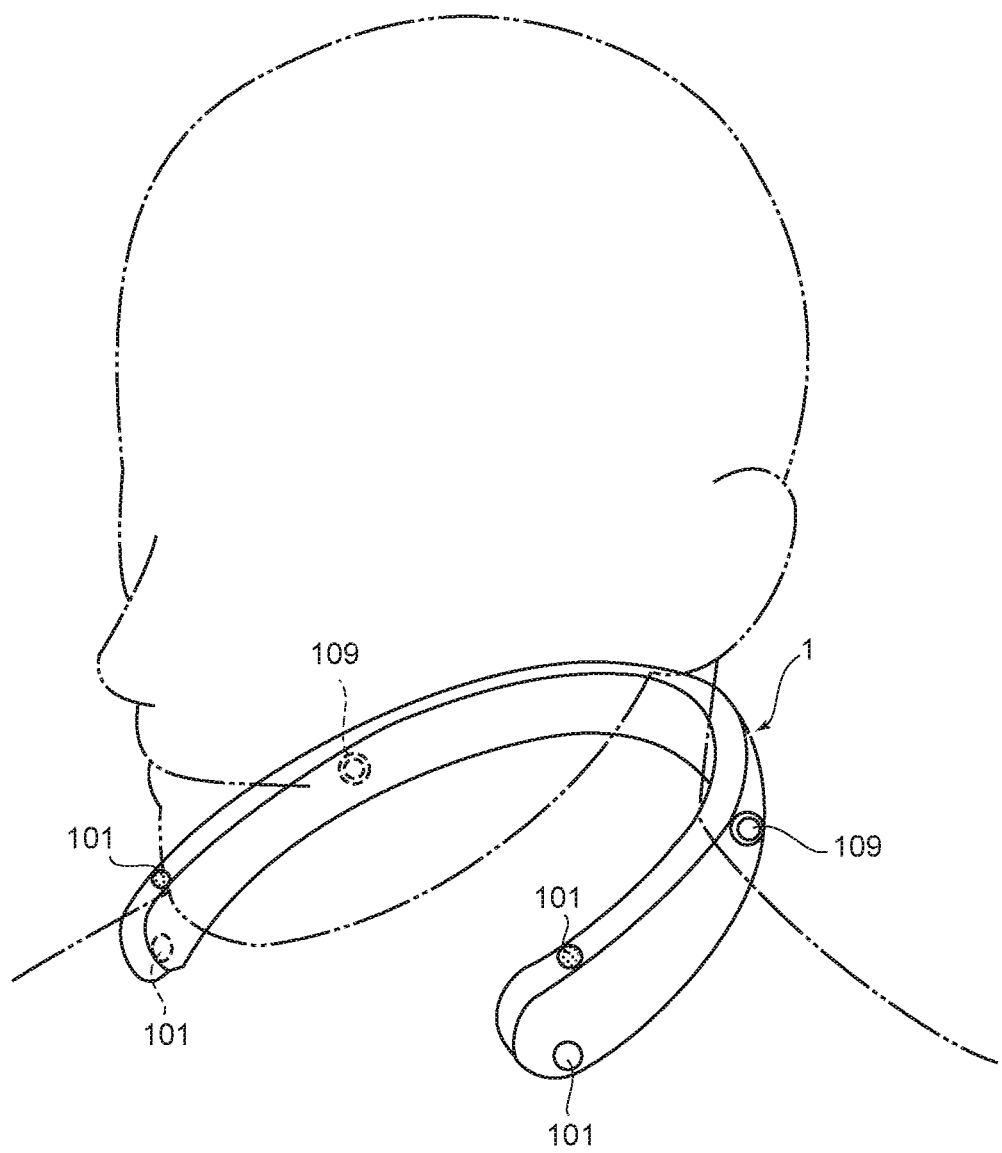
FIG. 3 is a diagram showing an example of an external configuration of the above-mentioned information processing apparatus.

FIG. 3 is a diagram showing an example of an external configuration of the information processing apparatus according to this embodiment. As shown in FIG. 3, the information processing apparatus 1 is, for example, a neckband-type wearable computer. As shown in FIG. 3, the neckband-type information processing apparatus 1 has a horseshoe shape as a whole, and a user wears it by hanging from the back side of the neck.

Further, as shown in FIG. 3, the information processing apparatus 1 includes an audio output unit 109 and various sensors 101. The audio output unit 109 reproduces audio data. In particular, a speaker 15 according to this embodiment reproduces an audio signal of a virtual object on which sound image localization processing has been performed, which causes the user to perceive the virtual object as if it were actually present in real space.

2-1. Internal Configuration

Figure 4:
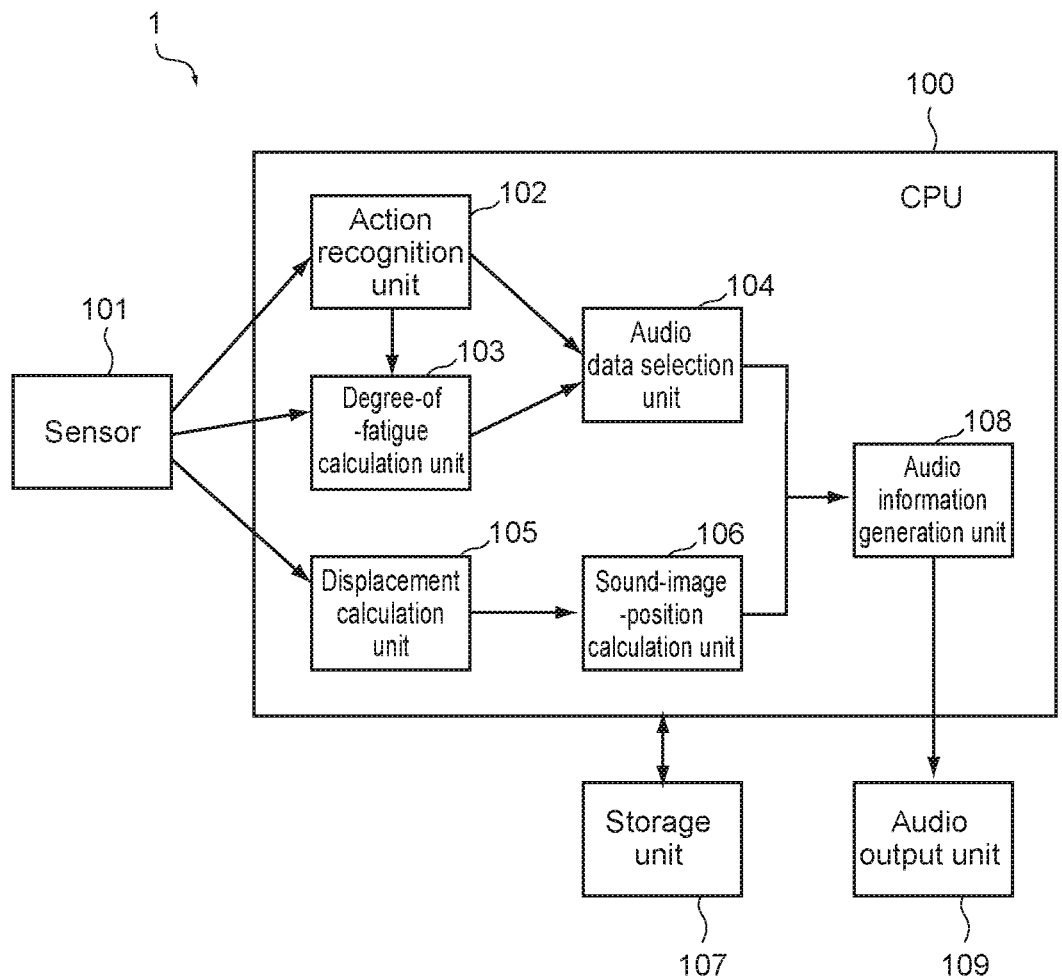
FIG. 4 is a block diagram showing an example of an internal configuration of the above-mentioned information processing apparatus.

FIG. 4 is a diagram showing an example of an internal configuration of the information processing apparatus according to this embodiment. As shown in FIG. 4, the information processing apparatus 1 includes, as hardware, a central processing unit (hereinafter, referred to as CPU) 100, the sensor 101, a storage unit 107, and the audio output unit 109. The CPU 100 is configured to have respective functional blocks as shown in FIG. 4 by information processing by a software program using this.

The sensor 101 is shown as an abstraction layer of various sensor device groups of the information processing apparatus 1. Specific examples of the sensor device include an acceleration sensor that detects acceleration in three directions of longitudinal, horizontal, and vertical directions, a gyro sensor that detects velocity around the axes in the three directions, a barometric pressure sensor that measures the atmospheric pressure, and an orientation sensor that detects geomagnetism. A mechanism for receiving a signal in a GPS (Global Positioning System), a mobile communication system, or a wireless local area network, and detecting position information (hereinafter, referred to as "absolute position information") of the information processing apparatus 1 may be regarded as one type of the sensor device group constituting the sensor 101. In addition, the specific examples of the sensor 101 include a sensor device that detects the pulse and body temperature of the user and an increase in the body temperature, and a microphone for inputting voice. Note that information input from the sensor 101 to the CPU 100 will be referred to as sensor information.

The storage unit 107 includes a non-volatile storage device such as an EEPROM (Electrically Erasable Programmable Read-Only Memory). The storage unit 107 stores a plurality of types of audio data.

The audio output unit 109 is a device having a function of outputting, as sound waves, multichannel audio information for localizing a sound image of a sound source in real space around the user, which is generated by an audio information generation unit 108. Specific examples thereof may include a speaker in the form as shown in FIG. 3.

The CPU 100 is an arithmetic processing device of the information processing apparatus 1. The CPU 100 does not necessarily need to be the main arithmetic processing device of the information processing apparatus 1. The CPU 100 may include an auxiliary device for the information processing apparatus 1. The CPU 100 executes a software program stored in the storage unit 107 or a software program downloaded from the outside. Accordingly, the CPU 100 is configured to include an action recognition unit 102, a degree-of-fatigue calculation unit 103, an audio data selection unit 104, a displacement calculation unit 105, a sound-image-position calculation unit 106, and the audio information generation unit 108 having the following functions.

The action recognition unit 102 recognizes the type of the action of the user as an example of an action pattern of the user.

The degree-of-fatigue calculation unit 103 is an example of a state analysis unit that analyzes the state of the user, and calculates the degree of fatigue of the user.

The audio data selection unit 104 selects appropriate audio data based on the type of the action of the user recognized by the action recognition unit 102 and the degree of fatigue calculated by the degree-of-fatigue calculation unit 103.

The displacement calculation unit 105 calculates, on the basis of the information input from the sensor 101, spatial displacement of the user, which occurs between a time T0 to a later time Tn.

The sound-image-position calculation unit 106 calculates, on the basis of the user displacement calculated by the displacement calculation unit 105, a position where a virtual object to be superimposed in real space should be localized in real space.

The audio information generation unit 108 generates multichannel audio information for localizing a sound image of a sound source in real space around the user by modulating the audio data selected by the audio data selection unit 104. At the time of modulation, the sound image position set by the sound-image-position calculation unit 106 is used as a parameter.

3. Operation

Figure 5:
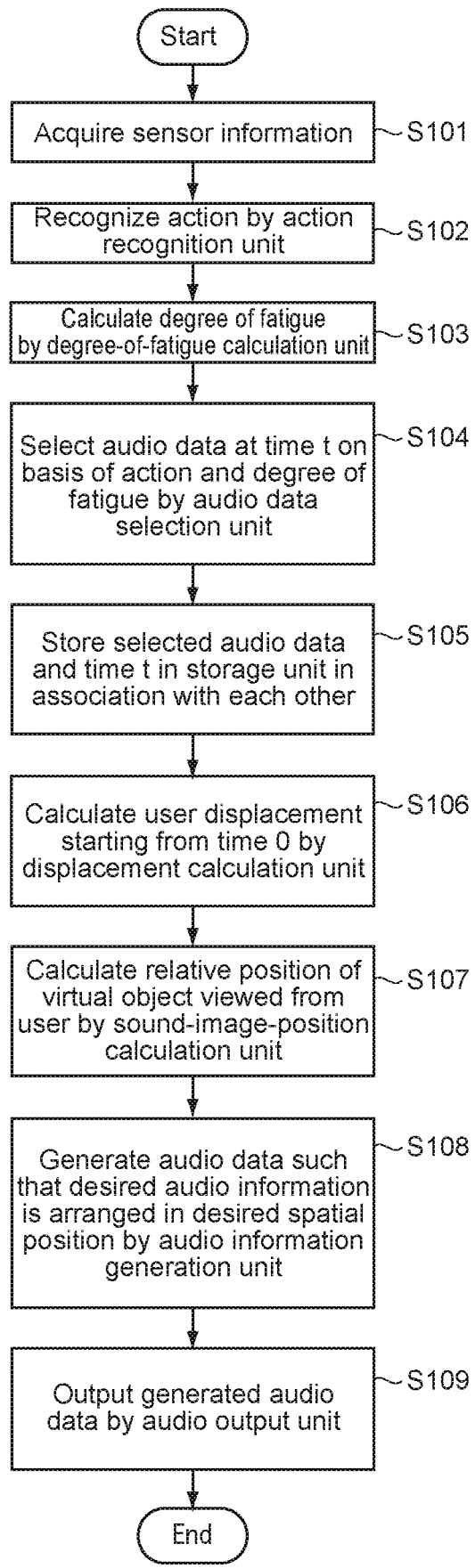
FIG. 5 is a flowchart showing a flow of processing executed by the above-mentioned information processing apparatus.

FIG. 5 shows a flow of processing executed by the information processing apparatus according to this embodiment. In the description of processing shown in FIG. 5 described below, unless otherwise noted, the CPU 100 is the main body of the operation. First, the CPU 100 acquires sensor information and inputs it to the respective units (S101).

Next, the action recognition unit 102 recognizes, on the basis of the information input from the sensor 101, the type of the action of an user (example of the action pattern of the user) (S102). Examples of the information processing of recognizing the type of the action include a method of using a learned determination device obtained by causing a determination device, which uses sensor information as input and the type of the action as output, to perform machine learning. Alternatively, a method of determining stationary/walking/running on the basis of a change in acceleration included in the sensor information may be used.

Next, the degree-of-fatigue calculation unit 103 calculates the degree of fatigue of the user (S103). The degree of fatigue of the user can be a parameter to accumulate. In this case, the parameter regarding the degree of fatigue is calculated by, for example, multiplying the degree of fatigue per unit time determined on the basis of the type of the action recognized by the action recognition unit 102 by the duration of the action. The degree of fatigue may be a parameter to gradually decrease over time.

For example, as the degree of fatigue per unit time, a value, e.g., $-\alpha$ for stationary, $+\beta$ for walking, and $+\gamma$ for running ($\alpha$, $\beta$, and $\gamma$ are positive values, $\beta<\gamma$), assigned for each type of the action by using the result of recognizing the action by the action recognition unit 102 may be used. Note that in the case where the type of the action of the user changes as a result of the action recognition, the degree of fatigue per unit time may be updated accordingly. The degree of fatigue may be calculated by integrating the degree of fatigue per unit time assigned in this way.

The degree-of-fatigue calculation unit 103 may calculate the degree of fatigue by a simpler method instead of the calculation of the degree of fatigue using the recognition result by the action recognition unit 102. For example, a value directly calculated from accumulation of the number of steps of the user, which is grasped by the sensor 101, or displacement detected by the acceleration sensor or gyro sensor may be output as the degree of fatigue. Alternatively, the activity amount based on the output of the sensor device that detects the pulse and body temperature of the user and an increase in the body temperature (example of sensor information) may be output as the degree of fatigue.

Next, the audio data selection unit 104 selects audio data in accordance with the type of the action of the user recognized by the action recognition unit 102 (S104). The storage unit 107 stores a plurality of patterns of audio data corresponding to the presumed types of the action in advance. A plurality of patterns of audio data may correspond to the type of one action. In this case, the audio data selection unit 104 randomly selects one of the plurality of patterns of audio data. Note that it does not necessarily need to select audio data, depending on the type of the action, e.g., in the case where outputting audio may cause the user to feel uncomfortable.

For example, in the case where the action recognition unit 102 has recognized that the action of the user is "walking", the audio data selection unit 104 randomly selects one of pieces of audio data associated with "walking" among motion sounds of the virtual object stored in the storage unit 107 in advance. In the case where the virtual object is a virtual dog as described above, audio that causes, if the user is walking, the user to feel as if the virtual dog were walking at the same pace as his/her pace is selected.

Similarly, the action recognition unit 102 has recognized that the action of the user is "running", the audio data selection unit 104 randomly selects one of pieces of audio data associated with "running" among motion sounds of the virtual object stored in the storage unit 107 in advance. Further, in the case where the action recognition unit 102 has recognized that the action of the user is "stationary", the audio data selection unit 104 randomly selects one of pieces of audio data associated with "stationary" among motion sounds of the virtual object stored in the storage unit 107 in advance. In the case of "stationary", it may be configured so as not to select audio data.

For example, audio data of footsteps or motion sounds when walking is associated with "walking". Audio data of footsteps when running or motion sounds that represent rougher breath than those when walking is associated with "running".

The audio data selection unit 104 selects audio data in accordance with also the degree of fatigue calculated by the degree-of-fatigue calculation unit 103 (S104). The audio data selection unit 104 divides the degree of fatigue into "large degree of fatigue" and "small degree of fatigue" by a predetermined threshold value. In the case where it is determined that the degree of fatigue is "large degree of fatigue", the audio data selection unit 104 randomly selects one of pieces of audio data associated with "large degree of fatigue" among motion sounds of the virtual object stored in the storage unit 108 in advance. Meanwhile, in the case where it is determined that the degree of fatigue is "small degree of fatigue", the audio data selection unit 104 randomly selects one of pieces of audio data associated with "small degree of fatigue" among motion sounds of the virtual object stored in the storage unit 108 in advance.

For example, a sound of shortness of breath may be associated with "large degree of fatigue". Further, the degree of fatigue may be divided into three or more levels such as large, medium, and small levels and grasped.

Figures 6A, 6B:
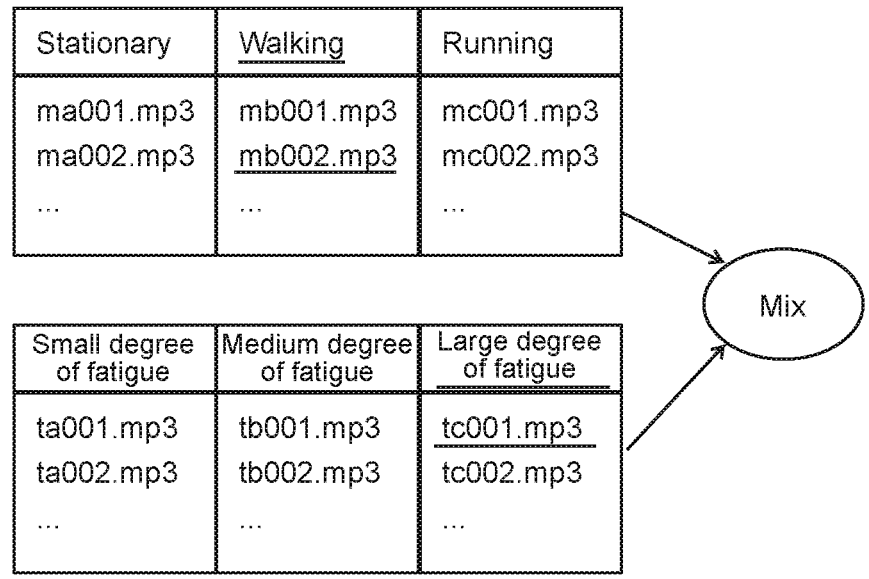
FIGS. 6A and 6B are diagrams describing information processing by an audio data selection unit of the above-mentioned information processing apparatus.

FIGS. 6A and 6B are explanatory diagrams for understanding information processing by the audio data selection unit 104. Two tables in FIG. 6A are a table showing the association between audio data of motion sounds or the like of the virtual object and the type of the action of the user and a table showing the association between audio data and the degree of fatigue, which are stored in the storage unit 107 in advance.

The audio data selection unit 104 selects audio data corresponding to the type of the action of the user recognized by the action recognition unit 102, selects audio data in accordance with the degree of fatigue calculated by the degree-of-fatigue calculation unit 103, and outputs the selected two pieces of audio data to the subsequent stage. In FIG. 6A, a file mb002.mp3 corresponding to "walking" and a file tc001.mp3 corresponding to "large degree of fatigue" are selected. The pieces of selected audio data are synthesized by the audio information generation unit 108.

As another example of the audio data selection by the audio data selection unit 104, a table as shown in FIG. 6B in which types of the action that can be recognized by the action recognition unit 102 and the degree of fatigue calculated by the degree-of-fatigue calculation unit 103 are combined may be prepared in advance, and processing of selecting the synthesized audio data may be performed. In this case, for example, as audio data corresponding to "walking" and "large degree of fatigue", "sound of walking while wheezing" or the like is placed.

As another example of the audio data selection by the audio data selection unit 104, there is an example in which the audio data selection unit 104 dynamically generates an audio data pattern and the dynamically-generated audio data is selected. In this case, the action of the user recognized by the action recognition unit 102 is a parameter having continuous values, and also the degree of fatigue calculated by the degree-of-fatigue calculation unit 103 is a parameter having continuous values. As described above, the audio data selection unit 104 may dynamically generate audio data on the basis of a parameter group including parameters of the degree of movement velocity from when "walking" to when "running" and the degree of fatigue.

In the case where audio data has been selected, the audio data selection unit 104 stores the pair of time and the selection result in the storage unit 107 (S105). The pair of time and the selection result is used by the sound-image-position calculation unit 106 and the like.

Next, the displacement calculation unit 105 calculates displacement starting from an arbitrary point in time (S106). The displacement calculated here represents spatial displacement of the information processing apparatus 1. Since it is premised that the user wears the information processing apparatus 1, hereinafter, the displacement calculated by the displacement calculation unit 105 will be referred to as "user displacement". The user displacement includes a relative change in the spatial position of the user, and also includes orientation, a horizontal position, a position in the vertical direction, and displacement thereof.

The displacement of the orientation can be calculated by, for example, integrating the output of the gyro sensor among pieces of sensor information input from the sensor 101. In addition, there is a method of acquiring the absolute orientation by the output of a geomagnetic sensor. In order to compensate for the accuracy of the geomagnetic sensor, the output of the gyro sensor may be integrated. By these methods, the displacement calculation unit 105 calculates the orientation (orientation of the user, front direction) among the user displacement.

The displacement calculation unit 105 calculates also the displacement of the horizontal position as one of the user displacement. The displacement of the horizontal position may be calculated by absolute position measurement that receives radio waves of a GPS satellite, or may be calculated by a method of performing wireless communication with a plurality of base stations to determine the absolute position. As another method, the displacement calculation unit 105 calculates the displacement of the relative position starting from a point in time on the basis of the travelling distance and the travelling direction (displacement of the orientation described above). Here, there is a method of obtaining the travelling distance by integrating the output value of the acceleration sensor.

Also, the travelling distance may be obtained by detecting the walking step from the change in acceleration and multiplying the step length corresponding to the walking step by the number of steps. In this case, as the step length, an average step length is fixedly used, or a step length is set by, for example, calculating the average step length of the user from the relationship between the horizontal moving distance and the number of steps.

The displacement calculation unit 105 calculates also the displacement of the height as one of the user displacement. The displacement in the height direction (vertical direction) can be calculated by a method of using the measurement value of the barometric pressure sensor or a method of calculating the displacement of the height corresponding to the case where it is recognized that the type of the action of the user recognized as "stand" and the type of the action of the user recognized as "sit" by the action recognition unit 102 are alternately repeated. Note that "stand"/"sit" can be recognized from the variation pattern of the measurement value of the acceleration sensor.

The user displacement calculated by the displacement calculation unit 105 is used by the sound-image-position calculation unit 106. The sound-image-position calculation unit 106 calculates the relative position of the virtual object viewed from the user (S107). This position is a sound source (position in real space) on the sense felt by the user due to the finally-synthesized audio in the case where the audio is output from the audio output unit 109.

Figure 7A:
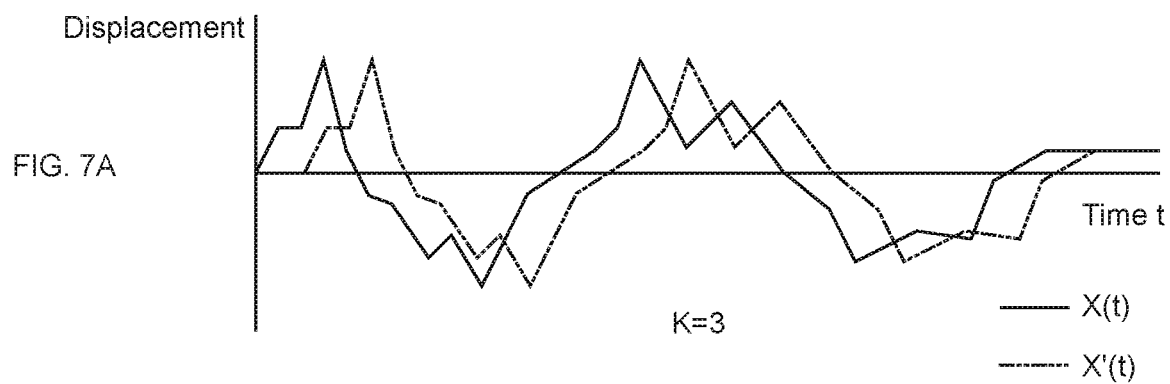
FIGS. 7A and 7B is a are diagrams describing information processing by a sound-image-position calculation unit of the above-mentioned information processing apparatus.
Figure 7B:
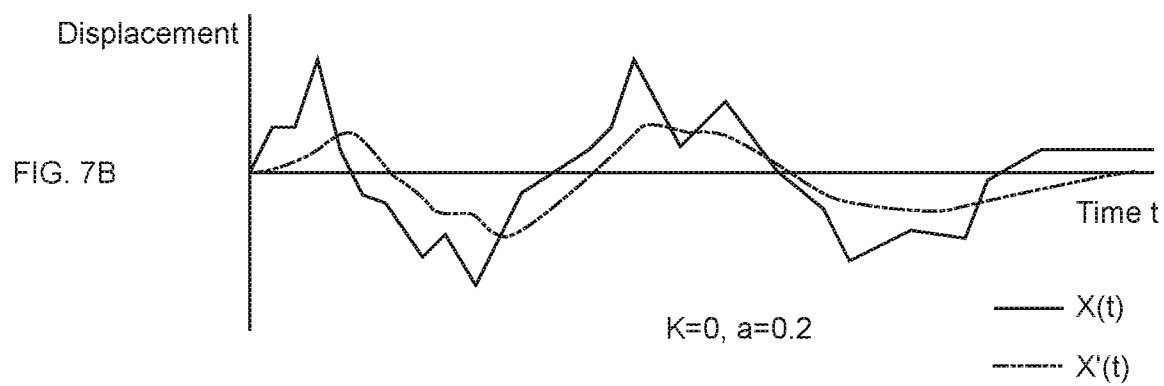

As the information processing by the sound-image-position calculation unit 106, appropriate one may be selected in accordance with the character that this application desires to give to the virtual object. In this case, several patterns are set in the calculation method executed by the sound-image-position calculation unit 106 in accordance with what character the virtual object is or what the virtual object is. Hereinafter, two representative patterns will be described with reference to FIGS. 7A and 7B. FIGS. 7A and 7B are schematic diagrams describing the information processing by the sound-image-position calculation unit 106, and illustrates the user displacement and displacement of the virtual object in respective patterns.

FIG. 7A shows a sound-image-position calculation pattern in which the movement of the virtual object traces the same position as that of the user displacement with a certain time delay. In the figure, the vertical axis is one-dimensional representation of six-dimensional information including three-axis positions and three-axis directions as an example of displacement. The horizontal axis represents a time t.

The sound-image-position calculation pattern in which user displacement can be tracked as shown in FIG. 7A can be achieved by, for example, the following formula. However, X(t) represents the user displacement, X'(t) represents the displacement of the virtual object, and K represents a time delay until the virtual object starts moving. The larger the value of K, the greater the time (delay) until it starts moving.

$$X'(t)=X(t-K)$$

The tracking of the user displacement by the virtual object as shown in FIG. 7A is effective in the case of presenting the existence that moves along the movement of the user. For example, in the case where it is desired to provide, to a user, augmented reality in which the virtual object is a human, robot, car, animal, or the like, i.e., the sound image localization position traces the same position as that of the user displacement with a certain time delay, such a sound-image-position calculation pattern may be adopted.

FIG. 7B shows a sound-image-position calculation pattern in which the virtual object moves so as to directly go to the position where the user is present with a certain time delay with respect to the user displacement. Such a sound-image-position calculation pattern can be achieved by, for example, the following formula. However, a represents the velocity of the movement of the virtual object. The closer the value of a, the longer it takes to catch up with the user. That is, the movement is slow.

$$X'(t)=aX(t-K)+(1-a)X'(t-1)$$

The tracking of the user displacement by the virtual object as shown in FIG. 7B is effective, for example, in the case of presenting the existence that follows the user through the wall. For example, it is suitable for expressing a ghost character as the virtual object.

The sound-image-position calculation unit 106 uses, as the position of the virtual object at the time t, the displacement X'(t) calculated by the above-mentioned information processing or the point at the time t that can be calculated thereby. Note that this point may be used as a base point, and a point obtained by adding a predetermined positional change to the base point may be used as the position of the virtual object. For example, in the case where the virtual object is a dog character, a point obtained by shifting the base point calculated by the calculation to a lower position closer to the ground is output. Alternatively, in the case where the virtual object is a ghost character, in order to produce a feeling of floating, calculations are made to add up and down positional changes at regular intervals. In accordance with this configuration, it is possible to reproduce more realistic movement of the character.

Further, the sound-image-position calculation unit 106 calculates the relative position of the character viewed from the user, taking into account the orientation displacement of the user for the position (X'(t)−X(t)) of the character with the user position as the starting point. As the sound image localization method, the method described in Patent Literature 1 can be used.

The audio information generation unit 108 performs information processing for spatially arranging audio information (S108). The information processing localizes a sound image at a relative position from the user such as a distance or direction from the user centering on the user, and the method as described in Patent Literature 1 can be used, for example.

The audio information generation unit 108 uses, as audio information to be used for output, the audio data selected by the audio data selection unit 104. However, in the case where there is a delay in the sound image position calculation, the selected audio data at the time when the user position is referred to is used. That is, in the case where the sound image position is calculated by the calculation formula of X'(t)=X(t−K), the audio data selected at the time t−K is used at the time t. The audio information generation unit 108 extracts and uses the audio data that is stored in association with the time information in the storage unit 107 by the audio data selection unit 104.

Further, the audio information generation unit 108 specifies, as the position (position where the sound image is localized) of the sound source on the sense felt by the user due to the output audio information, the position calculated by the sound-image-position calculation unit 106 on the basis of the user displacement output by the displacement calculation unit 105. The audio information generation unit 108 modulates the audio data so that it is heard from the specified position. In this embodiment, it is generated as 2-ch audio information. However, depending on the specific embodiment of the audio output unit 109, it may be generates as 5.1-ch audio information.

Further, the audio information generation unit 108 may adjust the reproduction speed of the modulated audio data in accordance with the moving velocity of the user calculated on the basis of the user displacement calculated by the displacement calculation unit 105. For example, even in the case where the audio data selected by the audio data selection unit 104 is the audio data corresponding to "walking" similarly, it is reproduced at the different reproduction speed depending on the difference of the moving velocity.

Next, the audio output unit 109 physically outputs, as sound waves, the audio data generated by the audio information generation unit 108 (S109).

4. Conclusion

In accordance with the above-mentioned embodiment, by recognizing the action pattern of a user and switching audio data to be reproduced on the basis thereof, it is possible to produce expression that follows the change in the action pattern of the user. Further, by changing the sound image localization position on the basis of the three-dimensional position or change in the orientation of the user, it is possible to produce sound expression that follows the result of the action of the user or the position where the user occupies in the space. Further, since the sound image localization position or base point thereof moves along with a predetermined delay from the action of the user, it is possible to produce sound expression that follows the positional change of the user. As described above, in accordance with the above-mentioned embodiment, in the case where a virtual character (e.g., dog) is set as the virtual object, sound expression as if it were actually present close to the user is realized.

5. Other Embodiments

Note that the present technology may also take the following configurations.

Although a neckband-type speaker hanging from the neck is shown as an appearance configuration example in FIG. 3, the technology disclosed in the above-mentioned embodiment is applicable also to other embodiments, e.g., a head mounted display including eyeglass-type one. In this case, it is also favorable to render the image at the position of the virtual object output through the information processing by the displacement calculation unit 105 and the sound-image-position calculation unit 106. A synergistic effect can be achieved by adding a visual stimulus to the auditory stimulus according to the present technology, and it is possible to provide augmented reality having higher quality to a user.

5-1. Another Embodiment 1

Figure 8:
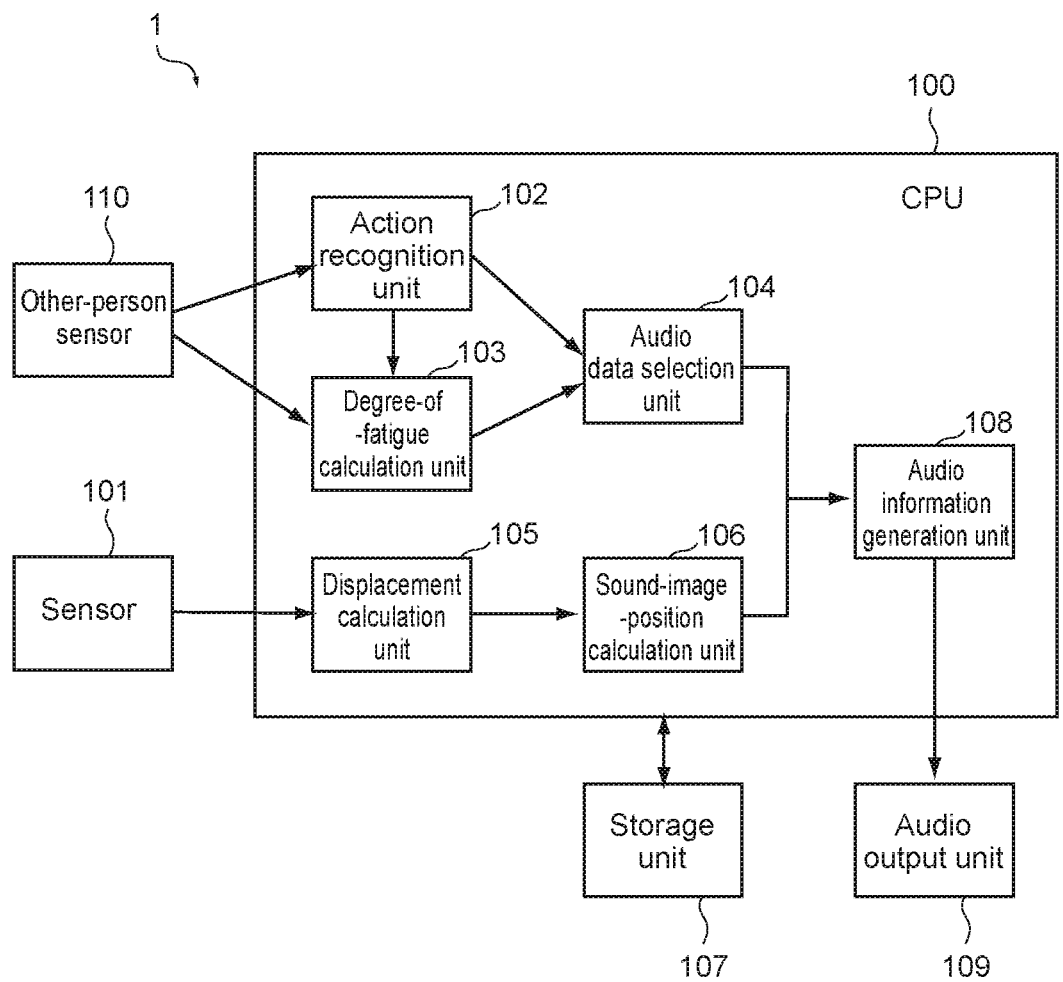
FIG. 8 is a block diagram showing an example of a configuration of another embodiment of the present technology.

The configuration of another embodiment 1 according to the present technology will be described with reference to FIG. 8. In this embodiment, assumption is made that there are a plurality of users of the information processing apparatus 1. In this embodiment, there are two types of sensor information to be input to the CPU 100. One or more sensors that output sensor information to be used in the information processing regarding the calculation of the user displacement by the displacement calculation unit 105 are set as the sensor 101, and one or more sensors that output sensor information to be used in the action recognition and the calculation of the degree of fatigue are set as an other-person sensor 110.

The displacement calculation unit 105 calculates the user displacement of the user who perceives the audio output by the audio output unit 109. The action recognition unit 102 and the degree-of-fatigue calculation unit 103 recognize, on the basis of sensor information of a different person who is not the user, the action pattern and degree of fatigue of the different person. Other information processing is similar to that in the above-mentioned embodiment.

In accordance with this embodiment, the action of the different user is recognized, the audio data according to the action pattern is selected, and the position in real space where the sound image is localized follows the spatial displacement of the user who listens to the audio. In accordance with this embodiment, it is possible to provide, to a user, augmented reality in which an avatar of the different person follows the user. The sound-image-position calculation unit 106 may set the sound image localization position in the air to produce a feeling as if the avatar of the different person floated.

This embodiment can be applied, but not limited, to a running application in which a user is capable of competing with another person running at a remote place. Alternatively, it may be applied to an application in which a user experiences the experience of another person. For example, by applying it to a head mounted display in which a user experiences another person's field of view, it is possible to provide, to the user, augmented reality in which he/she traces the movement of a remote athlete.

5-2. Another Embodiment 2

Figure 9:
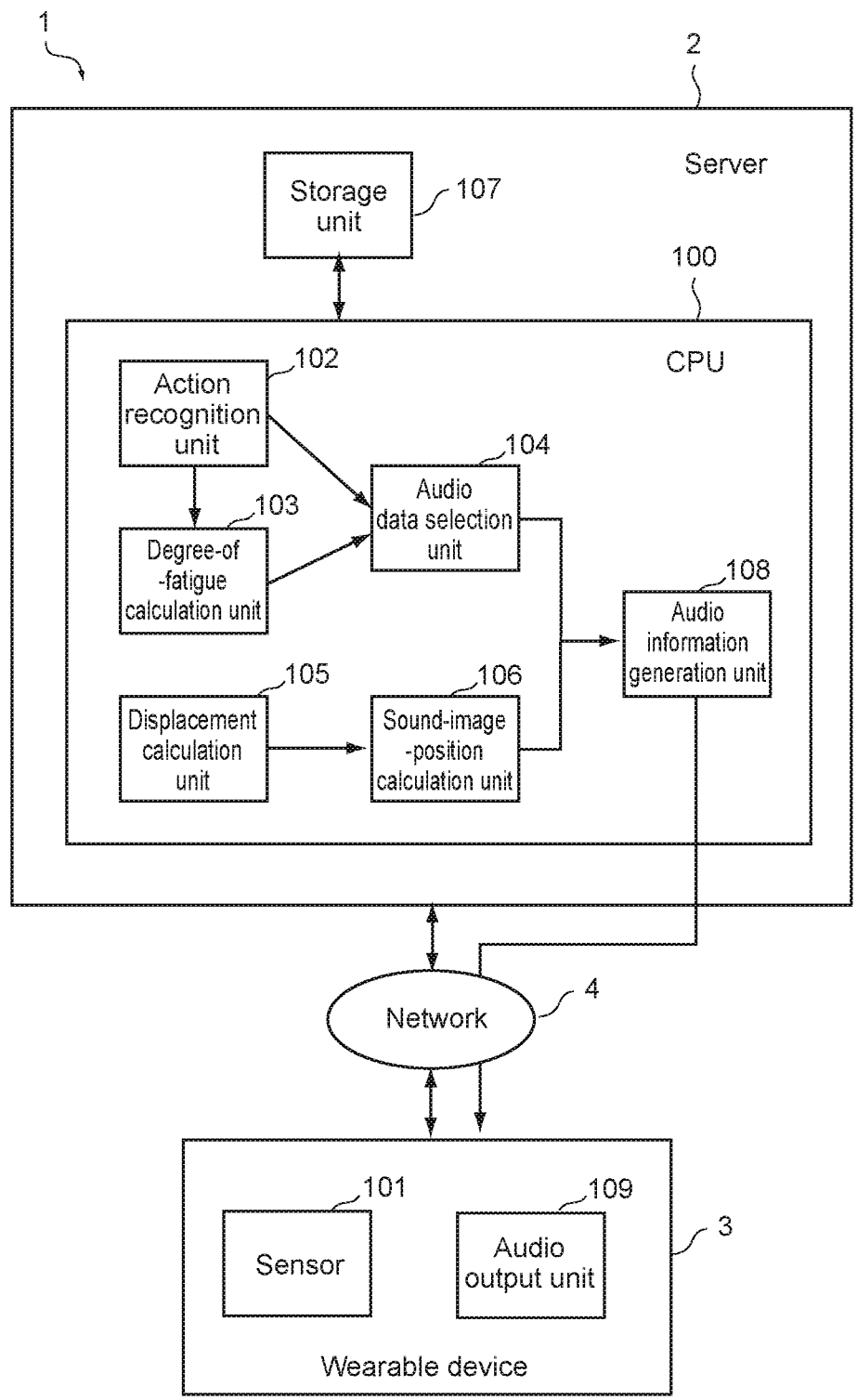
FIG. 9 is a block diagram showing an example of a configuration of another embodiment of the present technology.

The information processing described in the above-mentioned embodiment does not depend on, for execution, the hardware and software configuration illustrated in the above-mentioned embodiment. The present technology may be implemented in a form in which a part or all of the functional blocks shown in FIG. 4 are executed on separate hardware. As shown in FIG. 9, this embodiment is an embodiment in which the information processing apparatus 1 is configured as a server client system in which a server 2 including the CPU 100 and the storage unit 107, and a wearable device 3 communicate with each other via a network 4.

In this embodiment, as the wearable device 3, the neckband-type speaker as shown in FIG. 3 can be adopted. In addition, a smartphone can be used as an example of the wearable device 3. The server 2 is placed on the cloud, and the information processing according to the present technology is executed on the side of the server 2. The present technology can also be implemented in such a form.

5-3. Another Embodiment 3

In the above-mentioned embodiment, the action recognition unit 102 recognizes the type of the action of the user in S102 in FIG. 5. In this embodiment, when a change in the type of the action of the user is recognized here, the audio data selection unit 104 selects both audio data corresponding to the switching pattern of audio data from that before change to that after change, and the audio data after the change.

The timing of switching the audio data is the timing of starting or finishing of the action. For example, in the case where a character to be given to a virtual object is a "bell-attached character" and the type of the action changes from "running" to "stationary", the audio data selection unit 104 selects a jingle sound that sounds like jingling. The audio data selection unit 104 selects both the audio data corresponding to "stationary" and audio data regarding the jingle sound.

In accordance with such a configuration in which the audio data is selected corresponding to the change in the action of the character regarding the virtual object, it is possible to provide, to a user, augmented reality richer in entertainment or more realistic augmented reality.

In addition to the jingle sound, the audio data selection unit 104 may select, when the type of the action changes from "running" to "stationary", a dialogue indicating that the character is surprised. In this case, it is possible to produce an effect that the character regarding the virtual object is surprised when the running user suddenly stops. It is possible to make the character more lively, and provide augmented reality richer in entertainment to a user.

5-4. Another Embodiment 4

In the above-mentioned embodiment, the action recognition unit 102 recognizes the type of the action of the user in S102 in FIG. 5. In this embodiment, when a change in the type of the action of the user is recognized here, the CPU 100 performs predetermined condition determination relating to the type of the action after the change. In this condition determination, whether or not the type of the action after the change matches with the information associated with the virtual object is determined.

In the above-mentioned embodiment or this embodiment, augmented reality (AR) as if a virtual object followed a user is provided to the user. In this regard, depending on the type of the action of the user, also the audio emitted from the virtual object is changed if possible. The information processing apparatus 1 gives personality, features, possessions, and the like as a non-existent character to the virtual object. In the case where such information associated with the virtual object does not match with the type of the action after the change, augmented reality is reduced.

In this regard, in this embodiment, whether or not the type of the action after the change matches with the information associated with the virtual object. When performing condition determination regarding the matching, the audio data selection unit 104 may select predetermined audio data.

For example, in the case where the type of the action changes from "walking" to "riding a bicycle", the condition determination of whether or not the possessions of the character regarding the virtual object include "bicycle" is performed. In this example, the condition determination of whether or not the possessions include "bicycle" corresponds to determination of whether or not the type of the action after the change matches with the information associated with the virtual object.

In the case where the information (possessions of the character) associated with the virtual object does not include a bicycle as a result of the determination in this example, i.e., the character does not have a "bicycle", the audio data selection unit 104 does not select the audio data corresponding to the bicycle. Instead, a voice of the character murmuring "I also want to ride a bicycle" may be selected.

In accordance with such a configuration in which the timing of the utterance of the character regarding the virtual object is controlled, it is possible to provide, to a user, augmented reality richer in entertainment or realistic augmented reality.

5-5. Another Embodiment 5

In the above-mentioned embodiment, the fatigue or the degree of fatigue of the user has been calculated as an example of the state of the user, and used for selecting audio data. However, as another example of the state of the user, an emotion (e.g., delight, anger, sorrow, and pleasure emotions) of the user may be acquired by the sensor 101, and audio data may be selected on the basis of the emotion. The sensor 101 is not particularly limited. As long as the emotion of the user can be acquired from blood pressure or body temperature by a biometric sensing device, audio data may be selected on the basis of the emotion.

Further, environmental information around the user may be acquired instead of or in addition to the state or emotion of the user, and audio data may be selected on the basis of the environmental information. For example, in the case where rainfall is detected as the environmental information, the audio data selection unit 104 selects a sound walking on the water pool in accordance with this. In accordance with this configuration, it is possible to provide, to a user, augmented reality richer in entertainment or realistic augmented realty.

5-6. Another Embodiment 6

The sound-image-position calculation unit 106 may determine the position where the virtual object is placed on the basis of one or more of the following combinations.
Information acquired from the sensor 101
Information acquired from the outside (map data, etc.)
Information regarding personality or possessions given to a virtual object For example, in the case where the information processing apparatus 1 is capable of acquiring detailed map data and the absolute position of the user based on the user displacement calculated by the displacement calculation unit 105 is in the vicinity of the wall of a building, the sound-image-position calculation unit 106 places the virtual object so that it is not at the position facing the user across the wall. For example, in the case where the virtual object is a character such as a dog, since it is unnatural if the character enters the other side of the wall during walking, the sound-image-position calculation unit 106 places the virtual object so that it turns around to the side of the user if detailed map data can be acquired.

The map data that can be acquired from the outside includes not only the rough latitude and longitude of the building but also the position coordinates of the wall that demarcates the boundary between the building and the road or the like. In the case where the information processing apparatus 1 is capable of using such map data, it is possible to regard the building as the range surrounded by the position coordinates of the wall. In this regard, the sound-image-position calculation unit 106 arranges the sound image localization position of the virtual object to be determined on the basis of the user displacement output by the displacement calculation unit 105 in the range excluding the coordinate positions of the building. Specifically, for example, the virtual object is placed on the side of the road. Alternatively, the sound-image-position calculation unit 106 places the virtual object in the direction in which space is opened (e.g., direction in which there is a road).

Further, in this example, in the case where the virtual object collides with an object such as a wall of the building on the map data, audio data such as a collision sound may be reproduced. For example, in the case where the position of the virtual object placed by the sound-image-position calculation unit 106 overlaps with the coordinates of the positional range of the building, the audio information generation unit 108 reproduces the audio data such as a collision sound.

Note that a character given to the virtual object is a character that can pass through a wall such as a ghost, the sound-image-position calculation unit 106 may place the character on the other side of the wall. Further, a particular jingle sound may be played at the moment when it passes through the wall.

In accordance with the configuration of this embodiment, it is possible to provide, to a user, augmented reality richer in entertainment or realistic augmented reality.

5-7. Another Embodiment 7

In this embodiment, in addition to the configuration disclosed in the above-mentioned embodiment, the audio information generation unit 108 has a configuration in which different audio information is generated depending on the state of the action of the character regarding the virtual object. For example, when the action recognition unit 102 grasps that the action pattern of the user is running for a long time exceeding a predetermined threshold, the audio data selection unit 104 may select different audio data, and audio information to be finally generated by the audio information generation unit 108 may differ. In this case, the audio information generation unit 108 may switch the audio data to be selected by the audio data selection unit 104 from the normal audio data when running to, for example, the audio data indicating that the character is tired, which includes, for example, a sound of shortness of breath or a voice "tired".

In accordance with such a configuration, it is possible to produce an effect that also the character regarding the virtual object has an action state (tired, bored, etc.), and it is possible to provide, to a user, augmented reality richer in entertainment or realistic augmented reality.

6. Appendix

A part of the technical idea disclosed in the specification can be described as the following (1) to (11).

(1)

An information processing apparatus, including:

an action recognition unit configured to recognize an action pattern of a user on the basis of sensor information;

an audio data selection unit configured to select audio data corresponding to the action pattern of the user recognized by the action recognition unit; and an audio information generation unit that generates, on the basis of the audio data selected by the audio data selection unit, multichannel audio information for localizing a sound image of a sound source in real space around the user.

(2)

The information processing apparatus according to (1) above, in which the audio data selection unit is configured to select the audio data as audio emitted from a virtual object to be placed in the real space, and the audio information generation unit is configured to perform sound image localization by generating the multichannel audio information, the virtual object being placed at a position of the sound source by the sound image localization.

(3)

The information processing apparatus according to (1) or (2) above, in which the audio data selection unit is configured to select, when audio data to be selected is changed as a result of recognition by the action recognition unit, both audio data corresponding to a switching pattern of audio data from that before the change to that after the change, and the audio data after the change.

(4)

The information processing apparatus according to any one of (1) to (3) above, in which the audio data selection unit is configured to select, when audio data to be selected is changed as a result of recognition by the action recognition unit, audio data that matches with information associated with the virtual object where there is a plurality of pieces of audio data corresponding to an action pattern of the user.

(5)

The information processing apparatus according to any one of (1) to (4) above, further including a displacement calculation unit that outputs, on the basis of the sensor information, user displacement including a relative change in a position of the user.

(6)

The information processing apparatus according to (5) above, in which the audio information generation unit is configured to modulate, on the basis of the user displacement output by the displacement calculation unit, the audio data selected by the audio data selection unit, thereby to generate the multichannel audio information.

(7)

The information processing apparatus according to (6) above, in which the audio information generation unit is configured to modulate the audio data selected by the audio data selection unit so that the sound source whose sound image is localized by the multichannel audio information is placed at a position following the user displacement output by the displacement calculation unit, thereby to generate the multichannel audio information.

(8)

The information processing apparatus according to (7) above, in which the audio information generation unit is configured to generate the multichannel audio information so that the sound source whose sound image is localized by the multichannel audio information follows a position in space with a time delay, the position starting from a position of the user identified by the user displacement.

(9)

The information processing apparatus according to any one of (5) to (8) above, in which the audio information generation unit generates, on the basis of the user displacement output by the displacement calculation unit and map information including position coordinates of a building acquired from outside, the multichannel audio information so that the virtual object is not placed in a range of the position coordinates of the building included in the map information.

(10)

The information processing apparatus according to (9) above, in which the audio information generation unit generates, where the range of the position coordinates of the building included in the map information overlaps with a position where the virtual object is placed, the multichannel audio information including a collision sound.

(11)

The information processing apparatus according to any one of (1) to (10) above, further including a state analysis unit configured to analyze a changeable state of the user in accordance with one of the action pattern of the user recognized by the action recognition unit and the sensor information.

(12)

The information processing apparatus according to (11) above, in which the audio data selection unit is configured to select audio data corresponding to the action pattern of the user and audio data corresponding to the state of the user analyzed by the state analysis unit.

(13)

The information processing apparatus according to (12) above, in which the audio information generation unit is configured to synthesize the audio data corresponding to the action pattern of the user selected by the audio data selection unit and the audio data corresponding to the state of the user, thereby to generate the multichannel audio information on the basis of the synthesized audio data.

(14)

The information processing apparatus according to any one of (11) to (13) above, in which the state analysis unit is configured to assign a degree of fatigue per unit time in accordance with one of the action pattern of the user recognized by the action recognition unit and the sensor information, and accumulate the assigned degree of fatigue per unit time, thereby to calculate the degree of fatigue as the state of the user.

(15)

The information processing apparatus according to any one of (1) to (14) above, in which the audio data selection unit selects, where the action pattern of the user recognized by the action recognition unit continues exceeding a predetermined threshold value, audio data different from the audio data corresponding to the action pattern of the user recognized by the action recognition unit.

(16)

An information processing method, including:

an action recognition step of recognizing an action pattern of a user on the basis of sensor information;

an audio data selection step of selecting audio data corresponding to the action pattern of the user recognized by the action recognition step; and an audio information generation step of generating, on the basis of the audio data selected by the audio data selection step, multichannel audio information for localizing a sound image of a sound source in real space around the user.

(17)

A program that causes a computer to execute the steps of:

an action recognition step of recognizing an action pattern of a user on the basis of sensor information;

an audio data selection step of selecting audio data corresponding to the action pattern of the user recognized by the action recognition step; and an audio information generation step of generating, on the basis of the audio data selected by the audio data selection step, multichannel audio information for localizing a sound image of a sound source in real space around the user.

REFERENCE SIGNS LIST 1 information processing apparatus
100 CPU
101 sensor
102 action recognition unit
103 a degree-of-fatigue calculation unit (state analysis unit)
104 audio data selection unit
105 displacement calculation unit
106 sound-image-position calculation unit
107 storage unit
108 audio information generation unit
109 audio output unit
110 other-person sensor

The invention claimed is:

1. An information processing apparatus, comprising:
a central processing unit (CPU) configured to:
recognize an action pattern of a user based on sensor information;
calculate a degree of fatigue of the user based on the recognized action pattern of the user;
select each of first audio data corresponding to the recognized action pattern of the user and second audio data corresponding to the calculated degree of fatigue of the user;
synthesize the selected first audio data and the selected second audio data;
generate multichannel audio information for localization of a sound image of a sound source in real space around the user,
wherein the generation of the multichannel audio information is based on the synthesis of the selected first audio data and the selected second audio data;
recognize a change in the action pattern of the user; and
select each of third audio data and fourth audio data based on the recognition of the change in the action pattern of the user, wherein
the third audio data is different from the fourth audio data,
the fourth audio data corresponds to a change of the first audio data to the third audio data, and
the third audio data corresponds to the changed action pattern of the user.

2. The information processing apparatus according to claim 1, wherein
the selected first audio data corresponds to audio output from a virtual object to be placed in the real space, and
the CPU is further configured to execute, based on the multichannel audio information, sound image localization for placement of the virtual object at a position of the sound source.

3. The information processing apparatus according to claim 1, wherein
the selected third audio data corresponds to information associated with a virtual object, and
the selected third audio data comprises a plurality of pieces of audio data corresponding to the action pattern of the user.

4. The information processing apparatus according to claim 1, wherein the CPU is further configured to output, based on the sensor information, user displacement including a relative change in a position of the user.

5. The information processing apparatus according to claim 4, wherein the CPU is further configured to:
modulate the selected first audio data based on the user displacement; and
generate the multichannel audio information based on the modulation of the selected first audio data.

6. The information processing apparatus according to claim 5, wherein the CPU is further configured to modulate the selected first audio data for placement of the sound source at a first position that follows the user displacement.

7. The information processing apparatus according to claim 6, wherein
the CPU is further configured to generate the multichannel audio information so that the sound source follows a second position in space with a time delay, and
the second position corresponds to the position of the user.

8. The information processing apparatus according to claim 4, wherein
the CPU is further configured to generate, based on the user displacement and map information including position coordinates of a building acquired from outside, the multichannel audio information so that a virtual object is placed outside a range of the position coordinates of the building.

9. The information processing apparatus according to claim 8, wherein
the CPU is further configured to generate the multichannel audio information based on overlap of the range of the position coordinates of the building with a position of the virtual object, and
the generated multichannel audio information includes a collision sound.

10. The information processing apparatus according to claim 1, wherein the CPU is further configured to analyze a changeable state of the user based on the recognized action pattern of the user, and the changeable state of the user corresponds to an emotion of the user.

11. The information processing apparatus according to claim 10, wherein the CPU is further configured to select each of the first audio data corresponding to the action pattern of the user and fifth audio data corresponding to the changeable state of the user.

12. The information processing apparatus according to claim 11, wherein the CPU is further configured to:
synthesize the first audio data and the fifth audio data; and
generate the multichannel audio information based on the synthesis of the first audio data and the fifth audio data.

13. The information processing apparatus according to claim 10, wherein the CPU is further configured to:
assign a degree of fatigue per unit time based on each of the recognized action pattern of the user and the sensor information; and
calculate the degree of fatigue as the changeable state of the user based on multiplication of the assigned degree of fatigue per unit time with a duration of action of the user.

14. The information processing apparatus according to claim 1, wherein the CPU is further configured to select, based on the recognized action pattern of the user that exceeds a threshold value, fifth audio data different from the first audio data.

15. An information processing method, comprising:
recognizing an action pattern of a user based on sensor information;
calculating a degree of fatigue of the user based on the recognized action pattern of the user;
selecting each of first audio data corresponding to the recognized action pattern of the user and second audio data corresponding to the calculated degree of fatigue of the user;
synthesizing the selected first audio data and the selected second audio data;
generating multichannel audio information for localizing a sound image of a sound source in real space around the user,
wherein the generation of the multichannel audio information is based on the synthesis of the selected first audio data and the selected second audio data;
recognizing a change in the action pattern of the user; and
selecting each of third audio data and fourth audio data based on the recognition of the change in the action pattern of the user, wherein
the third audio data is different from the fourth audio data,
the fourth audio data corresponds to a change of the first audio data to the third audio data, and
the third audio data corresponds to the changed action pattern of the user.

16. A non-transitory computer-readable medium having stored thereon computer-executable instructions that, when executed by a processor, cause the processor to execute operations, the operations comprising:
recognizing an action pattern of a user based on sensor information;
calculating a degree of fatigue of the user based on the recognized action pattern of the user;
selecting each of first audio data corresponding to the recognized action pattern of the user and second audio data corresponding to the calculated degree of fatigue of the user;
synthesizing the selected first audio data and the selected second audio data;
generating multichannel audio information for localizing a sound image of a sound source in real space around the user,
wherein the generation of the multichannel audio information is based on the synthesis of the selected first audio data and the selected second audio data;
recognizing a change in the action pattern of the user; and
selecting each of third audio data and fourth audio data based on the recognition of the change in the action pattern of the user, wherein
the third audio data is different from the fourth audio data,
the fourth audio data corresponds to a change of the first audio data to the third audio data, and
the third audio data corresponds to the changed action pattern of the user.

* * * * *